(12) United States Patent
Roby

(10) Patent No.: US 6,558,409 B1
(45) Date of Patent: May 6, 2003

(54) PLASMA TREATED SURGICAL NEEDLES AND METHODS FOR THEIR MANUFACTURE

(75) Inventor: Mark S. Roby, Killingworth, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 0 days.

(21) Appl. No.: 09/966,661

(22) Filed: Sep. 28, 2001

(51) Int. Cl.⁷ .............................. A61B 17/04
(52) U.S. Cl. ........................................ 606/222
(58) Field of Search ........................ 606/222; 528/25, 528/31, 32, 28; 427/447, 489; 204/165

(56) References Cited

U.S. PATENT DOCUMENTS

| | | | |
|---|---|---|---|
| 3,187,752 A | 6/1965 | Glick | 128/335.5 |
| 3,280,160 A | 10/1966 | Bailey | 260/448.2 |
| 3,297,033 A | 1/1967 | Schmitt | 128/335.5 |
| 3,527,650 A | 9/1970 | Block | 117/7 |
| 3,541,127 A | 11/1970 | Beattle et al. | 260/448.8 |
| 3,629,310 A | 12/1971 | Bailey | 260/448.8 R |
| 3,755,399 A | 8/1973 | Nitzsche et al. | 260/448.8 R |
| 3,837,891 A | 9/1974 | Teitz | 117/46 FA |
| 3,839,297 A | 10/1974 | Wasserman et al. | 260/78.3 R |
| 3,942,523 A | 3/1976 | Rudtke | 128/132 D |
| 4,105,304 A | 8/1978 | Baker | 351/47 |
| 4,184,004 A | 1/1980 | Pines et al. | 442/102 |
| 4,185,637 A | 1/1980 | Mattei | 606/230 |
| 4,207,071 A | 6/1980 | Lipowitz et al. | 8/115.6 |
| 4,217,228 A | 8/1980 | Koerner et al. | 252/8.84 |
| 4,283,519 A | 8/1981 | Pines et al. | 528/26 |
| 4,359,545 A | 11/1982 | Ona et al. | 252/8.61 |
| 4,429,080 A | 1/1984 | Casey et al. | 525/415 |
| 4,557,946 A | * 12/1985 | Sacher et al. | 427/489 |
| 4,578,116 A | 3/1986 | Rott et al. | 106/18.12 |
| 4,617,340 A | 10/1986 | Tanaka et al. | 524/588 |
| 4,624,676 A | 11/1986 | White et al. | 8/115.56 |
| 4,699,967 A | 10/1987 | Eichenauer et al. | 528/29 |
| 4,784,665 A | 11/1988 | Ona et al. | 8/115.6 |
| 4,937,277 A | 6/1990 | O'Lenick, Jr. | 524/318 |
| 5,019,093 A | 5/1991 | Kaplan et al. | 606/228 |
| 5,059,213 A | 10/1991 | Chester field et al. | 606/228 |
| 5,338,770 A | 8/1994 | Winters et al. | 523/112 |
| 5,383,903 A | 1/1995 | Totakura | 606/228 |
| 5,463,010 A | 10/1995 | Hu et al. | 528/25 |
| 5,541,167 A | 7/1996 | Hsu et al. | 514/56 |
| 5,955,588 A | 9/1999 | Tsang et al. | 536/21 |

OTHER PUBLICATIONS

Kim et al. "Thermal and Structural Analysis of Heparin--PEO-PDMS-PEO-Heparin Pentablock Copolymers", Journal of Applied Polymer Science 1994, 54(12), 1863–1872.

H. Yasuda, "Plasma Polymerization", Academic Press, Inc, pp. 1–431 (1985).

* cited by examiner

Primary Examiner—Gary Jackson

(57) ABSTRACT

Methods for siliconizing surgical needles include a plasma polymerization coating process.

48 Claims, 1 Drawing Sheet

PLASMA TREATED SURGICAL NEEDLES AND METHODS FOR THEIR MANUFACTURE

BACKGROUND

1. Technical Field

The present disclosure generally relates to siliconized surgical needles. More particularly, the present disclosure is directed to siliconized surgical needles having reduced tissue penetration force and methods for making such needles employing a plasma polymerization process for the application of a siliconization material.

2. Background of Related Art

The use of plasma polymerization processes to form membranes or coatings on the surfaces of substrates is known in the art. For example, U.S. Pat. No. 5,463,010 discloses substrates coated with membranes formed by the plasma polymerization of hydrocyclosiloxane monomers that possess enhanced hydrophobicity, thromboresistance, gas permeability and biocompatibility. U.S. Pat. No. 5,650,234 discloses carbonate compounds that may be bound to amine groups on a polymeric surface formed by the plasma polymerization of hydrocyclosiloxane monomers. These carbonate compounds may then be bound to bioactive compounds.

Other examples of plasma coating processes include U.S. Pat. Nos. 5,182,317 and 5,338,770 which disclose methods for producing thrombo-resistant coatings on biomedical devices and implants wherein the surface to be coated is subjected to plasma polymerization in order to create a siloxane surface onto which a plurality of amine functional groups have been bonded, reacting the amine functional groups with polyethylene oxide chains, and then reacting bioactive molecules with the polyethylene oxide chains.

The siliconization of metallic cutting edges of articles such as, for example, razor blades, hypodermic needles, scissors, scalpels, and curettes, is also known. For example, Dow Corning Corporation's Dow Corning® MDX4-4159 Fluid has been used to siliconize cutting edges with an ambient temperature and humidity-curable mixture of an aminoalkyl siloxane and a cyclosiloxane dissolved in a mixture of Stoddard solvent and isopropyl alcohol.

Other examples include U.S. Pat. Nos. 5,258,013 and 5,458,616 which disclose coating surgical needles with a siliconization material containing an aminoalkyl siloxane and a cyclosiloxane employing ultrasonic radiation. The siliconization material can be applied in a solvent carrier, e.g., hexane or heptane.

Yet another example is U.S. Pat. No. 5,985,355, which discloses coating surgical needles by (1) coating the needle with a coating solution comprising a highly condensable polydimethylsiloxane in a solvent to form a leveling coat; (2) evaporating the solvent from the first coating; (3) curing the leveling coating to polymerize the polydimethylsiloxane; (4) applying a second coating solution over the leveling coat comprising a polydimethylsiloxane having amino and alkoxy functional groups and a solvent; and (5) evaporating the solvent from the second coating.

The previously known processes for siliconizing needles produce surgical needles in which the force of penetration is clearly reduced compared with untreated needles. However, in these needles, the force of penetration increases considerably when a tissue is pierced several times in succession with the same needle, as happens frequently in practice during operations.

It would be advantageous to provide siliconized surgical needles which continue to exhibit significantly reduced penetration force upon successive passes through tissue during a suturing operation.

SUMMARY

It has been discovered that subjecting a surgical needle to a plasma polymerization process for the application of a silicone coating can provide a siliconized surgical needle in which the needle exhibits an average tissue penetration force below that of a standard siliconized surgical needle.

In a preferred embodiment, the surgical needle is first subjected to a plasma etching process with an ammonia and oxygen plasma to activate the surface of the needle. The needle is then subjected to a plasma polymerization process whereby aliphatic hydrocyclosiloxane monomers are polymerized on the surface of the needle to form a siloxane coating on the needles. In one embodiment, amine groups are introduced onto the polymer coating by co-polymerizing an organo-based monomer with the aliphatic hydrocyclosiloxane monomer or by carrying out a second plasma polymerization process for the introduction of the organo-based monomer. The amine groups on the polymer coating may then be reacted with carbonate polyoxyalkylenes to give polyoxyalkylene modified polymer coatings that exhibit enhanced lubricity.

After the formation of the polymer coating, the needles may then be coated with a lubricant composition. In one embodiment, the lubricant composition includes an aminoalkyl siloxane and at least one other siloxane such as a cyclosiloxane which is copolymerizable therewith. In another embodiment, the lubricant composition is a mixture that includes at least one polydialkylsiloxane having a molecular weight sufficient to provide a viscosity of the mixture of at least about 10,000 cp and at least one other siliconization material. In yet another embodiment, the lubricant composition includes a polydialkylsiloxane and at least one siliconization material which does not covalently bond with the polydialkylsiloxane. In a preferred embodiment, the lubricant composition is applied to a needle possessing a polyoxyalkylene modified polymer coating.

The expression "standard siliconized surgical needle" or "standard needle" as used herein refers to a commercially available siliconized surgical needle, e.g., the siliconized surgical needles attached to sutures marketed by Ethicon, Inc. (Somerville, N.J.).

While the amount of force required to achieve penetration of tissue during suturing may initially be about the same for the siliconized surgical needle of this disclosure and a presently available siliconized surgical needle, and while both needles will tend to experience an increase in penetration force with each successive passage through tissue, at the conclusion of any given number of such passages the siliconized needle of this disclosure will exhibit significantly less penetration force than the presently available needle. Thus, the siliconized needle of this disclosure will advantageously retain its initial tissue penetration characteristics to a greater extent than a presently available siliconized needle in a manner which is particularly advantageous, as it reduces the effort required in the suturing operation.

DESCRIPTION OF THE PREFERRED EMBODIMENTS

Figure 1:
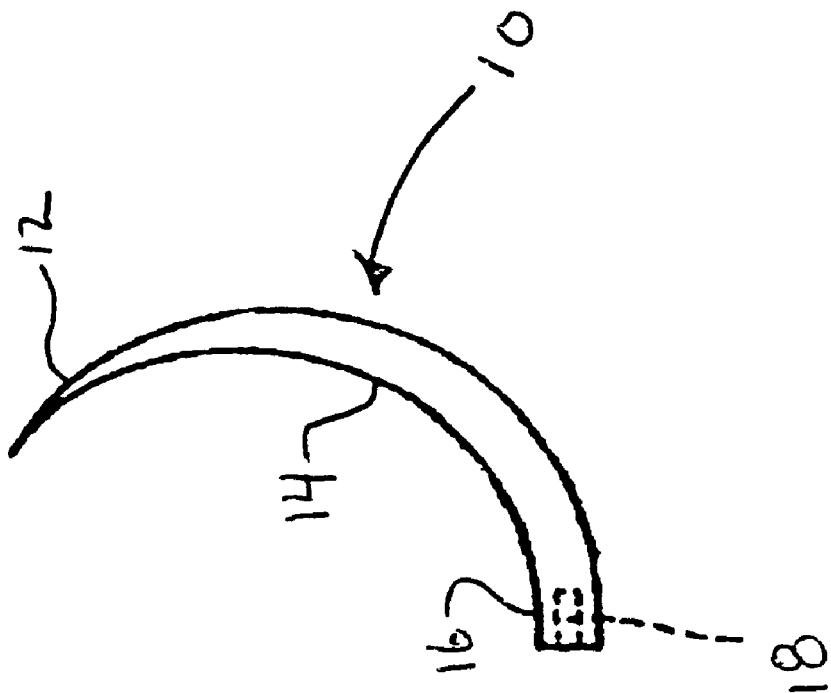
FIG. 1 depicts a surgical needle treated in accordance with the present disclosure.

Preferred embodiments of the present disclosure involve the use of plasma polymerization processes to produce siliconized surgical needles. It has been discovered that using a plasma polymerization process to apply a silicone coating will produce a siliconized surgical needle which exhibits a significantly reduced tissue penetrating force after a number of passages through tissue. Thus, the average tissue penetration force of the siliconized needle herein will advantageously be less than about 10%, preferably less than about 20% and more preferably less than about 30%, of the average tissue penetration force of a standard siliconized needle from after about 5 to about 20 passes through the same or similar tissue.

As seen in FIG. 1, a surgical needle 10 generally includes a tip portion 12, a body portion 14 and a needle attachment portion 16. The coatings described herein can be applied to needles of any configuration. Thus the needle may be curved, straight or have a compound configuration. The cross section of the needle can be round, oval, triangular, rectangular, or any other geometry. The needle may include cutting edges. The tip portion may be pointed or blunt. The suture attachment portion can be, e.g., an eye, a slot or, as shown in FIG. 1, a bore 18.

Surgical needles which can be treated and coated in accordance with this disclosure can be manufactured from a variety of metals. Such metals include, but are not limited to, Series 400 and Series 300 stainless steels, and the quaternary alloys disclosed in U.S. Pat. Nos. 3,767,385 and 3,816,920, the contents of which are incorporated by reference herein.

In general, needles to be treated in accordance with the present disclosure are subjected to a plasma polymerization process to form a polymer coating on the needle surface. The term "plasma" refers to a thermodynamically non-equilibrium gaseous complex, composed of electrons, ions, gas atoms, free radicals, and molecules in an excited state, known as the plasma state.

Plasma may be generated in a process known as plasma discharge by a number of methods including combustion, flames, electric discharges, controlled nuclear reactions and shocks. The most obvious and commonly used is electric discharge. Radio frequency ("RF") or microwave discharge are mainly used for polymerization reactions. For commercial RF generators, the frequency used in the process is dictated by the Federal Communications Commission and is set at 13.56 MHz.

Two opposing processes occur simultaneously during plasma discharge. In general, it can be said that the generation of free radicals in the vapor phase leads to the formation of thin films. However, at high power of field strength, ions are generally responsible for ablation or "etching" of the surface of any article introduced into the plasma. At very low gas or monomer flow rates, there is little polymer deposition and the deposition rate decreases with increasing discharge power. At higher flow rates, the deposition of polymer increases (linearly), but reaches a maximum with increasing discharge power and then ablation becomes more predominant.

There are two types of commercially available plasma-state polymerization systems: (a) capacitively coupled internal parallel electrodes, such as Bell Jar reactors, and (b) RF coil-inductively coupled tubular reactors. Generally, without modification, these systems are not suitable for producing the uniform single-phase coatings at high enough deposition rates for processing large quantities of needles and are more suitable for controlled etching of needle surfaces.

The most serious shortcoming of the above-mentioned commercial systems for polymer formation is their inability to control the monomer flow to the region between the electrodes. This inability renders it impossible to achieve uniform plasma density, plasma composition, or deposition rate between the electrodes. Furthermore, because the monomer is not confined to the electrode region in these systems, the flow rate between the electrodes is significantly decreased. In addition, because of the undirected monomer flow, oily and powdery deposits of plasma polymerized monomers form throughout the plasma chamber. One way to eliminate these deposits is by restricting the flow path in the reactor chamber to the space between the electrodes, which maintains polymer deposition solely in the plasma glow zone. Thus, when the plasma glow zone is activated, the monomer or monomer mixture is continually passed through the plasma glow zone and the unused monomer or monomer mixture condenses in the cold trap.

In order to adequately form polymers on the needle surface, one must understand the limitations of the commercially available systems noted above and the parameters which affect the formation of a plasma coating or membrane. The relationship between the plasma intensity, free radical concentration, and system pressure is complex. The plasma coating parameter-formula, W/FM, where W is the RF power, F is the monomer flow rate, and M is molecular weight of the monomer (see Yasuda, H., Plasma Polymerization, Academic Press, 1985) fails to address two important factors: system pressure and the plasma reactor geometry.

At a given W and F, if the system pressure increases above a given pressure, the resulting coating is no longer homogenous and a two-phase morphology coating will start to appear. This two-phase phenomenon is caused by an increase in the system pressure which decreases the mean free path of monomer free radicals and results in the monomer free radicals recombining in the gas phase before reaching the needle surface. This in turn results in deposition of plasma polymerized siloxane powder along with polymerization of free radicals on the needle surface, resulting in the two-phase coating. The W/FM parameters also will change when the geometry of the plasma reactor changes. Therefore, W/FM can be a useful plasma coating parameter only if the system is maintained at constant pressure and only if the same plasma reactor geometry is utilized.

A plasma coating system with the same reactor geometry can be used if the W/FM formula is employed as a control indicator. If the system is controlled at a given pressure, increasing W and decreasing F will likely result in etching or ablation of the needle surface. If W is decreased and F is increased, the desired coating will most likely result.

In accordance with the present disclosure, needles may first be subjected to plasma etching to activate the surface of the needle prior to the plasma polymerization process. The intensity of the non-polymer forming plasma (i.e., plasma etching) is dependent on the combined factors of pressure and discharge power as well as on other factors of the discharge system such as distance between electrodes, surface area of electrodes, and total volume of the reactor.

In a preferred embodiment, an ammonia/oxygen plasma is used for the etching process. The ammonia component of the above plasma etching process modifies the needle surface and introduces nitrogen to the surface. The oxygen component of the plasma etching process generates highly reactive species that react with the ammonia and the surface of the needle.

In one embodiment, the plasma chamber used for plasma etching has capacitively coupled plate-type electrodes. The needles are exposed to ammonia having a mass flow rate in the range from about 10 to about 70 standard cubic centimeters per minute (sccm) and oxygen having a mass flow rate from about 2 to about 20 sccm, at an absolute pressure in the range from about 20 mTorr to about 100 mTorr. The exposure time ranges from about 10 seconds to about 15 minutes. The currently preferred exposure time is in the range from about 15 seconds to about 90 seconds. A radio frequency of 13.56 MHz in the range from about 20 watts to about 250 watts generates sufficient energy to break the molecular bonds of the ammonia and oxygen gases.

It will be appreciated by those skilled in the art that in a differently configured plasma chamber, the ammonia and oxygen flow rate, power, chamber pressure, and exposure time may be outside the ranges of that set forth for the embodiment discussed above.

Where needles to be treated in accordance with the present disclosure are not subjected to plasma etching, or in those cases where they have been subjected to the plasma etching process described above, a polymer coating is applied to the needle surface by a plasma polymerization process. The monomers used to form the polymer coating are polymerized directly on the needle surface using plasma-state polymerization techniques generally known to those skilled in the art. See Yasuda, Plasma Polymerization, Academic Press Inc., New York (1985), incorporated herein by reference.

In brief, the monomers are polymerized onto the needle surface by activating the monomer in a plasma state. The plasma state generates highly reactive species, which form the characteristically highly cross-linked and highly-branched, ultra-thin polymer coating, which is deposited on the needle surface as it moves through the area of the reactor having the most intense energy density, known as the plasma glow zone.

For plasma polymerization to produce a coating on a needle, which may also be called "plasma grafting", a suitable organic monomer or a mixture of monomers having polymerizable unsaturated groups is introduced into the plasma glow zone of the reactor where it is fragmented and/or activated forming further excited species in addition to the complex mixture of the activated plasma gases. The excited species and fragments of the monomer recombine upon contact with the needle surface to form a largely undefined structure which contains a complex variety of different groups and chemical bonds and forms a highly crosslinked polymer coating on the needle surface. If $O_2$, $N_2$, or oxygen or nitrogen containing molecules are present, either within the plasma reactor during the polymer coating process, or on exposure of the polymer coated needle to oxygen or air subsequent to the plasma process, the polymeric deposit will include a variety of polar groups.

The amount and relative position of polymer deposition on the needles is influenced by at least three geometric factors: (1) location of the electrodes and distribution of charge; (2) monomer flow; and (3) needle position within the reactor relative to the glow region.

Modifications of the monomer flow rate and flow path are factors in avoiding two-phase coatings and obtaining the necessary high deposition rates of plasma polymerized coatings on needle surfaces. In general, a high flow rate (about 1 μmole/sec to about 10 μmole/sec), moderate R.F. power (about 20 to about 120 W), and low system pressure (about 10 to about 70 mTorr) will produce a suitable homogeneous siloxane coating.

During the plasma polymerization process, the needle is subjected to both thermal and ultra-violet (UV) radiation. The heat generated can be removed by external fans constantly blowing onto the system. The heat generated by electrons, ions, or free radicals colliding with the needle surface is insignificant and will not effect the bulk mechanical properties of the needle. The total energy released as heat or mechanical energy after impact is relatively small but the surface of the needle may become chemically active and unstable.

In practice, an electric discharge from an RF generator is applied to the "hot" electrodes of a plasma reactor. The selected monomers are introduced into the reactor and energized into a plasma, saturating the plasma glow zone with an abundance of energetic free radicals and lesser amounts of ions and free electrons produced by the monomers. As the needle passes through or remains in the plasma glow zone, the surface of the needle is continually bombarded with free radicals, resulting in the formation of the polymer coating.

In accordance with the present disclosure, siloxane monomers are used in the plasma polymerization process to produce polymer coatings on the needle surfaces.

One preferred polymer coating which can be deposited on the needle surface through the plasma state polymerization process of the present disclosure uses aliphatic hydrocyclosiloxane monomers of the general formula:

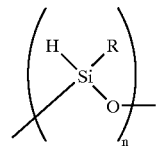

where R is an aliphatic group and n is an integer from 2 to about 10, preferably 4 to 6. Preferred aliphatic hydrocyclosiloxane monomers include: 1,3,5,7-tetramethylcyclotetrasiloxane ("TMCTS"); 1,3,5,7,9-pentamethylhydrocyclopentasiloxane ("PMCTS"); 1,3,5,7,9,11-hexamethylhydrocyclohexasiloxane ("HMCHS") and a mixture of 1,3,5,7,9-pentamethylcyclopentasiloxane and 1,3,5,6,9,11-hexamethylcyclohexasiloxane monomers ("XMCXS"). Use of a radio frequency power greater than 5 W, a system pressure less than 300 mTorrs, and a monomer flow rate greater than 1 μmole/sec, will cause a homogeneous, hard, hydrophobic, biocompatible, polymer coating with a low friction coefficient to form on the needle surface passing through the plasma glow zone.

The aliphatic hydrocyclosiloxane monomers noted above may be used to create a homogeneous coating on the needle surface. In another embodiment, the aliphatic hydrocyclosiloxane monomers may be mixed with co-monomers to give polymer coatings having properties different from the properties of the homogenous coating. For example, by introducing reactive functionalizing monomers, or organo-based monomers, or fluorocarbon monomers together with the aliphatic hydrocyclosiloxane monomers in the plasma polymerization system, physical pore size and chemical affinity of the plasma copolymerized aliphatic hydrocyclosiloxane coating with selective monomers can be controlled. This allows the use of the copolymerized plasma polymer coating for applications which require the coating to differentiate between certain types of gases, ions, and molecules and it also may be utilized to introduce functional groups to the polymer coating which, in turn, can help link other compounds or compositions to the polymer coating.

In a preferred embodiment, the polymer coatings may be produced by a plasma co-polymerization process of mixtures of the same aliphatic hydrocyclosiloxane monomers noted above with organo-based monomers that introduce amine groups onto the polymer coating and form amine grafted polymer coatings. It is more preferred to introduce these organo-based monomers onto the polymer coating in a second plasma grafting process which occurs after the plasma polymerization of the aliphatic hydrocyclosiloxane monomers. Suitable organo-based monomers include allylamine, N-trimethylsilylallylamine, unsaturated amines (both N-protected and N-unprotected), and cyclic aliphatic amines (both N-protected and N-unprotected). As used herein, the term "amine grafted polymer coatings" refers to a polymer coating containing amine groups, which can be obtained either by co-polymerization of the organo-based monomer with the hydrocyclosiloxane monomer or by plasma grafting the organo-based monomer onto a previously formed siloxane polymer coating.

In yet another embodiment, these plasma treated needles, possessing amine grafted polymer coatings, are then reacted with carbonate-based polyoxyalkylene compounds to produce polyoxyalkylene modified polymer coatings. In a preferred embodiment, the carbonate-based polyalkylene oxide is of the general formula

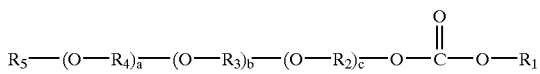

wherein $R_1$ is an N-benzotriazole group, an N-2-pyrrolidinone group, or a 2-oxypyrimidine group; $R_2$, $R_3$ and $R_4$ are independently selected alkylene groups of about 2 to about 3 carbon atoms and may be the same or different; $R_5$ is selected from hydrogen, methyl, a carbonyloxy-N-benzotriazole group, a carbonyloxy-N-2-pyrrolidinone group, and a carbonyl-2-oxypyrimidine group; a is an integer from 1 to 1000 and each of b and c is an integer from 0 to 1000, where a+b+c is an integer from 3 to 1000. Suitable lower alkylene groups include those having about 2 to about 3 carbon atoms.

In preferred compounds of the above formula, $R_2$, $R_3$ and $R_4$ is —($CH_2CH_2$)— or —$CH_2CH(CH_3)$— or any combination thereof. More preferably $R_2$, $R_3$ and $R_4$ are ethylene. According to a preferred aspect a, b, and c are selected so as to give a molecular weight for the PEG moiety of about 500 to about 20,000, more preferably from 3000 to 4000. Preferred polyoxyalkylene carbonates include, but are not limited to, polyoxyethylene bis-(2-hydroxypyrimidyl) carbonate, polyoxyethylene bis-(N-hydroxybenzotriazolyl) carbonate and polyoxyethylene bis-(N-hydroxy-2-pyrrolidinonyl) carbonate.

These polyoxyalkylene modified polymer coatings have enhanced lubricity and possess a polyoxyalkylene tether capable attaching additional compounds, including lubricants, to the polymer coating.

An important feature of the present invention is the creation of a continuous thin coating. The thickness of this coating can be determined gravimetrically, and the continuity of the coating can be determined by its permeability. These factors, along with the chemical composition of the coating (i.e., carbon, silicone, oxygen, nitrogen percentages), determined by ESCA (electron spectroscopy for chemical analysis) are some of the values which change as plasma parameters are modified.

Surgical needles which can be coated in accordance with this disclosure can be manufactured from a variety of metals. Such metals include, for example, Series 400 and Series 300 stainless steels. Other suitable metals for the fabrication of surgical needles include the quaternary alloys disclosed in U.S. Pat. Nos. 3,767,385 and 3,816,920, the contents of which are incorporated by reference herein. A preferred quaternary alloy possesses the ranges of components set forth below in Table I:

TABLE I

COMPOSITION OF SURGICAL NEEDLE QUATERNARY ALLOY (WT. %)

| Component(s) | Broad Range | Preferred Range | Most Preferred Range |
|---|---|---|---|
| Nickel | 10–50 | 24–45 | 30–40 |
| Cobalt | 10–50 | 25–45 | 30–40 |
| Nickel + Cobalt | 50–85 | 60–80 | 65–75 |
| Chromium | 10–30 | 12–24 | 15–22 |
| Molybdenum, tungsten and/or niobium (columbium) | 5–20 | 8–16 | 10–13 |

Another preferred quaternary alloy within Table I which can be utilized for the siliconized needle of this disclosure, designated MP35N, is available in wire form from Maryland Specialty Wire, Inc. (Cockeysville, Md.) and contains (nominal analysis by weight): nickel, 35%; cobalt, 35%; chromium, 20% and molybdenum, 10%.

It is preferred to apply a lubricant composition to the plasma treated needles in order to further enhance their lubricity. The lubricant coating may be applied to at least the tip portion of the needle possessing a polymer coating in accordance with the present disclosure. In particularly useful embodiments, the entire needle receives the lubricant composition. Where the lubricant composition is curable, it may be necessary to avoid filling or blocking any eye, slit or bore present at the suture attachment portion of the needle.

While the lubricant may be applied to needles having just the siloxane polymer coating or the amine grafted polymer coating, in a preferred embodiment the lubricant composition is applied to a needle possessing a polyoxyalkylene modified polymer coating.

The lubricant composition includes at least one silicone material. As used herein, the term silicone means silicones and derivatives of silicone chemistry, including but not limited to silicone fluids, silicone oils, silicone-organic copolymers, silicone resins, volatile silicones (cyclomethicones), linear silicones, cyclosiloxanes, polydialkylsiloxanes, polydimethylsiloxanes, dimethicone copolyols, silicone glycols, aminofunctional silicones, polymeric silicones, silicone waxes, such as high molecular weight dimethicones, and silicone derivative waxes.

In one embodiment, the lubricant composition is Dow Corning® MDX 4-4159 Fluid ("MDX Fluid"), a 50 percent active solution of dimethyl cyclosiloxanes and dimethoxysilyldimethylaminoethylaminopropyl silicone polymer in a mixture of Stoddard solvent (mineral spirits) and isopropyl alcohol. It is preferred to apply the MDX Fluid to the polymer coated surgical needle by dipping, wiping, spraying, etc. in the form of a first dilute organic solution, e.g., prepared with a solvent such as, for example, a hydrocarbon solvent possessing from about 5 to about 10 carbon atoms, e.g., pentane, hexane, heptane, octane, etc., trichlorotrifluoroethane, 1,1,1-trichloroethane, mineral spirits, alcohols, e.g., isopropyl alcohol, and the like and mixtures thereof. It is preferred to dilute MDX Fluid (or other siliconization material) with hexane and isopropyl alcohol with MDX-Fluid being present in the concentration range of from about 10 g/l to about 80 g/l and preferably from about 20 g/l to about 40 g/l.

In a particularly useful embodiment, the lubricant composition is a mixture containing at least a polydialkylsiloxane having a molecular weight sufficient to provide a viscosity of the coating mixture of at least about 10,000 cp and at least one siliconization material followed by curing.

Suitable polydialkylsiloxanes for use in forming the coating mixture herein include polydimethylsiloxanes, polydiethylsiloxanes, polydipropylsiloxanes, polydibutylsiloxanes and the like with polydimethylsiloxanes being preferred.

In a particularly useful embodiment, the lubricant composition includes a mixture of an aminoalkyl siloxane and at least one other copolymerizable alkylpolysiloxane. Particularly preferred polydimethylsiloxanes are polydimethylsiloxanes having a molecular weight sufficient to provide a viscosity of the coating mixture of at least about 10,000 cp and preferably of at least about 30,000 cp. Such polydimethylsiloxanes for use herein are the products sold by Dow Corning under the name "Syl-Off DC 23", which is suitable as a high density condensable polydimethylsiloxane, and NuSil Technology under the name "MED1-4162" (30,000 cp).

Suitable siliconization materials for addition with the foregoing polydialkylsiloxanes to form the coating mixtures of this disclosure include siliconization materials containing an aminoalkyl siloxane and at least one other copolymerizable siloxane, e.g., an alkylpolysiloxane or a cyclosiloxane; a silicone oil, e.g., one sold by Dow Corning Corporation under the name Dow 36 Medical Fluid (350 to 12,500 centistokes), and the like with the siliconization material containing an aminoalkyl siloxane and at least one other copolymerizable siloxane being preferred. Generally, the preferred siliconization material includes (a) from about 5 to about 70 weight percent of an aminoalkyl siloxane of the general formula

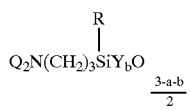

wherein R is a lower alkyl radical containing no more than about 6 carbon atoms; Y is selected from the group consisting of —OH and —OR' radicals in which R' is an alkyl radical of no more than about 3 carbon atoms; Q is selected from the group consisting of hydrogen, —CH$_3$ and —CH$_2$CH$_2$NH$_2$; a has a value of 0 or 1, b has a value of 0 or 1 and the sum of a+b has a value of 0, 1 or 2; and (b) from about 30 to about 95 weight percent of a methyl substituted siloxane of the general formula

wherein R" is selected from the group consisting of —OH and —CH$_3$ radicals and c has a value of 1 or 2. The two components of this siliconization material copolymerize, forming a lubricating coating on the surface of the needle.

In addition to, or in lieu of, the foregoing second copolymerizable siloxane, one can use one or more cyclosiloxanes such as, e.g., those described in the "Encyclopedia of Polymer Science and Engineering", Mark et al., eds., 2$^{nd}$ ed., Vol. 15, John Wiley & Son (1989), p. 207 et seq., the contents of which are incorporated by reference herein, provided, of course, the total amount of the second copolymerizable siloxane(s) is within the aforestated range.

A particularly preferred siliconization material for use herein in combination with the aforementioned polydimethylsiloxane(s) to form the coating mixture is MDX Fluid, which, as noted above, is an active solution of dimethyl cyclosiloxanes and dimethoxysilyldimethylaminoethylaminopropyl silicone polymer in a mixture of Stoddard solvent (mineral spirits) and isopropyl alcohol. Another preferred siliconization material is NuSil Technology's MED-4159.

In one embodiment of the present disclosure, the coating mixture can be formed by adding a first solution of at least one of the foregoing polydialkylsiloxanes in a solvent with a second solution of at least one of the foregoing siliconization materials in a solvent. Under preferred conditions, the first solution can be prepared by adding Syl-Off DC 23, MED1-4162 or both in a solvent such as, for example, a hydrocarbon solvent having from about 5 to about 10 carbon atoms, e.g., pentane, hexane, heptane, octane, etc., xylene, chlorinated solvents, THF, dioxanone and the like and mixtures thereof with hexane being preferred. The first solution is typically formed from Syl-Off DC 23 or MED1-4162 with hexane with Syl-Off DC 23 or MED1-4162 being present in the concentration range of from about 10 g/l to about 70 g/l and preferably from about 35 g/l to about 45 g/l.

The second solution, also under preferred conditions, can be prepared in the form of a dilute organic solution, e.g., one prepared with a solvent such as, for example, a hydrocarbon solvent possessing from about 5 to about 10 carbon atoms, e.g., pentane, hexane, heptane, octane, etc., trichlorotrifluoroethane, 1,1,1-trichloroethane, mineral spirits, alcohols, e.g., isopropyl alcohol, and the like and mixtures thereof. It is preferred to dilute MDX Fluid (or other siliconization material) with hexane and isopropyl alcohol with MDX Fluid being present in the concentration range of from about 10 g/l to about 80 g/l and preferably from about 20 g/l to about 40 g/l. In a preferred embodiment, the siliconization material is a mixture of MED1-4162 and MDX Fluid.

The mixture will ordinarily be formed by adding the first solution of the polydialkylsiloxane in solvent with the second solution of the siliconization material in solvent in a ratio ranging from about 12:1 to about 1:12, preferably from about 6:1 to about 1:6 and more preferably from about 2:1 to about 1:2. As one skilled in the art will readily appreciate, the amount of the first and second solutions necessary in forming the mixtures herein will vary depending on the volume of mixture desired.

Once the coating mixture is formed, it can then be applied to the foregoing needles employing techniques known to one skilled in the art, e.g., by dipping, wiping, spraying, total immersion, etc, with dipping and spraying being the preferred techniques. Preferably, the plasma treated needles are dipped into the coating mixture for about 5 to about 60 seconds, preferably about 10 to about 45 seconds and more preferably from about 15 to 30 seconds to form a coating on the needles. After evaporation of any dilutant or solvent carrier, the siliconized coating is cured to the desired degree.

The coating can be cured by, for example, first placing the coated needle in a humid environment, e.g., a humidification chamber, and exposing the coated needle to a temperature of from about 10° C. to about 50° C. and preferably from about 20° C. to about 35° C. in a relative humidity of from about 20% to about 80% and preferably from about 50% to about 65%. The coated needles are subjected to the foregoing temperatures and humidities to initiate curing to the desired degree and provide an improved lubrication coating. Typically, a time period ranging from about 1 hour to about 6 hours and preferably from about 2 hours to about 4 hours is employed. The coated needles are then placed in, e.g., furnace or oven, and cured by heating the needles to a temperature of from about 100° C. to about 200° C., preferably from about 110° C. to about 150° C. and more preferably from about 115° C. to about 150° C. for a time period ranging from about 2 hours to about 48 hours and preferably from about 15 hours to about 25 hours such that cross-linking of the polydialkylsiloxane and siliconization material occurs. In a particularly useful embodiment, the coated needles are heated to a temperature of 140° C. for 4 hours and a temperature of 120° C. for 20 hours.

In another embodiment of the present disclosure, the coating mixture herein is formed from at least a polydialkylsiloxane and a siliconization material which does not covalently bond with the polydialkylsiloxane. A suitable polydimethylsiloxane for use herein which does not covalently bond with the siliconization material is a product sold by NuSil Technology under the name "MED-4162". Generally, the mixture is formed by adding a first solution containing at least the polydimethylsiloxane in a solvent with the second solution discussed hereinabove. The first solution is preferably formed employing the polydimethylsiloxane MED-4162 in a solvent such as, for example, a hydrocarbon solvent having from about 5 to about 10 carbon atoms, e.g., pentane, hexane, heptane, octane, etc., xylene, and the like and mixtures thereof with hexane being preferred. It is particularly preferred to form the first solution from MED-4162 in hexane in generally the same ranges as the first solution discussed above and then adding the first solution and second solution in generally the same ratios as discussed above to form the coating mixture. Once the mixture is formed, it can then be applied to the surface of a surgical needle employing generally the same techniques and parameters as discussed above. The coating mixture is then subjected to curing conditions, e.g., the curing steps discussed above, such that the siliconization material polymerizes and cross-links thereby interlocking the polydimethylsiloxane in the coating resulting in an interpenetrating networked coating.

The following non-limiting examples are illustrative of the siliconized surgical needles and the method for their manufacture of the present disclosure.

EXAMPLE 1

This experiment compared the penetration forces required for needles treated in accordance with the present disclosure and needles coated with standard silicone coatings as a control. Surgical needles made of stainless steel were supplied by United States Surgical (Norwalk, Conn.). Care was taken to minimize handling of the needles, and whenever possible the needles were handled with plastic forceps. The control needles were coated with Dow Corning® MDX 4-4159 Fluid.

Needles treated in accordance with the present disclosure were treated with a mixture of $NH_3/O_2$ for 45 seconds in a glow-discharge plasma. The plasma was generated at 110 W under a pressure of 50 mTorr and a mass flow rate of 40 sccm (standard cubic centimeter per minute) for $NH_3$ and 10 sccm for $O_2$. The ammonia modified and introduced nitrogen to the needle surface. The oxygen generated highly reactive species that reacted with the ammonia and the surface of the needles.

After the above plasma etching, the siloxane derivative, 1,3,5,7-tetramethylhydrocyclotetrasiloxane (TMCTS, Hydrosilox®) was polymerized on the needle surfaces in a plasma deposition lasting for varying amounts of time, forming siloxane-coated needles. The TMCTS plasma was generated at 83 W, 55 mTorr, and a flow rate of 84 sccm.

N-trimethylsilyl allylamine (TMSAA) was then plasma grafted to the siloxane-coated needle at 65 mTorr, 35 W, and a flow rate of 42 sccm. This process introduced an amine functionality to the coating that was subsequently modified in the next step.

Polyethylene oxide compound (PEOC) was used to prepare a bifunctional-crosslinker polyoxyethylene bis-(N-hydroxybenzotriazolyl) carbonate (HPEOC). HPEOC was then conjugated to the surface-bound primary amines of the coated needle during a 10 minute immersion in a solvent. During the conjugation, hydroxybenzotriazolyl carbonate was liberated and polyoxyethylene-(N-hydroxybenzotriazolyl) attached to the amine via a urethane bond. Thereafter, the needles were rinsed extensively to remove unbound materials and heat dried.

Subsequent to the above treatment, some of the needles were coated with a silicone coating of Dow Corning® MDX 4-4159 Fluid.

Good results were seen with the plasma coated (45 second Etch; 2 minute TMCTS; 4 minute TMSAA, followed by conjugation with HPEOC) needles which were re-coated with Dow Corning® MDX 4-4159 Fluid. This resulted in an average 24% reduction in force of the first pass needle penetration (with respect to the silicone coated needle control); and an average of 35% reduction in force during the $8^{th}$ pass. The overall average result of all 8 passes (combined) was a 33% force reduction. Needles that were coated in accordance with the above process, with the only difference being that no silicone coating was applied after attachment of the polyoxyalkylene carbonate, were found to require penetration forces roughly equivalent to the silicone coated needles used as a control.

EXAMPLE 2

Electron spectroscopy for chemical analysis (ESCA) data was obtained for stainless steel wafers coated pursuant to the plasma polymerization process described above in Example 1 and is presented below in Table 1. ESCA collects data over a small spot size to a depth of approximately 50 Å. The studies were conducted to determine the composition of the coating after the plasma deposition step. The post TMSAA data includes wafers subjected to an initial treatment with $NH_3/O_2$ plasma, TMCTS, and TMSAA.

TABLE 1

| | COMPOSITION IN ATOMIC % | | | | |
|---|---|---|---|---|---|
| | Fe | Cr | O | N | C |
| stainless steel | 13.7 | 1.3 | 61 | 0 | 25 |
| post TMSAA | 1.6 | 0.1 | 33.5 | 5.7 | 40 |

The following Table 2 provides contact angle data for the stainless steel wafers coated pursuant to the steps described above in Example 1. The standard deviation for each condition was obtained from 5 wafers.

TABLE 2

| SPECIMEN | DESCRIPTION | CONTACT ANGLE |
|---|---|---|
| 1 | Siloxane coating, thin | 101° ± 2° |
| 2 | Siloxane coating, thick | 102° ± 1° |
| 3 | Thin PEOC over siloxane | 52° ± 3° |
| 4 | Thick PEOC over siloxane | 51° ± 5° |
| 5 | Siloxane coating, thin (short etch) | 102° ± 1° |
| 6 | PEOC followed by $O_2$ plasma | 35° ± 4° |

It will be understood that various modifications may be made to the embodiments disclosed herein. Therefore, the above description should not be construed as limiting, but merely as exemplifications of preferred embodiments. For example, metal surfaces other than needles can be coated with the coating mixture in accordance with the methods described herein. Those skilled in the art will envision other modifications within the scope and spirit of the claims appended hereto.

What is claimed is:

1. A method for coating a surgical needle comprising the steps of:
   providing a surgical needle having a surface; and
   forming a polymer coating on at least a portion of the surface of the needle by plasma polymerization of a hydrocyclosiloxane monomer of the general formula

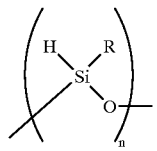

where R is an aliphatic group and n is an integer from 2 to about 10, preferably 4 to 6,
   whereby the polymer coated needle exhibits reduced penetration force compared to an uncoated needle.

2. The method of claim 1 wherein said hydrocyclosiloxane monomer is selected from the group consisting of 1,3,5,7-tetramethylcyclotetrasiloxane; 1,3,5,7,9-pentamethylhydrocyclopentasiloxane; 1,3,5,7,9,11-hexamethylhydrocyclohexasiloxane and a mixture of 1,3,5,7,9-pentamethylcyclopentasiloxane and 1,3,5,6,9,11-hexamethylcyclohexasiloxane monomers.

3. The method of claim 1 further comprising the step of adding an amine group onto the polymer coating by subjecting the needle to a gas containing a monomer selected from the group consisting essentially of unsaturated N-protected amines, unsaturated N-unprotected amines, N-protected cyclic aliphatic amines, and N-unprotected cyclic aliphatic amines, to produce an amine grafted polymer coating.

4. The method of claim 3 wherein the unsaturated or cyclic amine is copolymerized with the hydrocyclosiloxane monomer onto the needle surface.

5. The method of claim 3 wherein the unsaturated or cyclic amine is plasma grafted onto the polymer coating on the needle surface.

6. The method of claim 3 wherein said unsaturated or cyclic amine is N-trimethylsilylallylamine.

7. The method of claim 3 further comprising the step of contacting the amine grafted polymer coating with a carbonate-based polyalkylene oxide compound.

8. The method of claim 7 wherein the carbonate-based polyoxyalkylene oxide compound is a compound of the formula

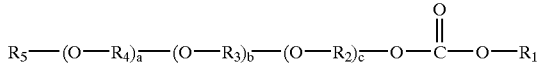

wherein $R_1$ is selected from an N-benzotriazole group, an N-2-pyrrolidinone group, or a 2-oxypyrimidine group; $R_2$, $R_3$ and $R_4$ are independently selected alkylene groups of about 2 to about 3 carbon atoms and may be the same or different; $R_5$ is selected from hydrogen, methyl, a carbonyloxy-N-benzotriazole group, a carbonyloxy-N-2-pyrrolidinone group, and a carbonyl-2-oxypyrimidine group; a is an integer from 1 to 1000 and each of b and c is an integer from 0 to 1000, where a+b+c is an integer from 3 to 1000 to produce a polyoxyalkylene modified polymer coating.

9. The method of claim 8 wherein said carbonate-based polyalkylene oxide compound is polyoxyethylene bis-(N-hydroxybenzotriazolyl) carbonate.

10. The method of claim 1 further comprising the step of subjecting the needle surface to plasma etching prior to the plasma polymerization process.

11. The method of claim 10 wherein the plasma etching comprises treating the needle surface with an ammonia/oxygen plasma.

12. The method of claim 1 further comprising the step of applying a lubricant composition over the plasma polymerized polymer coating.

13. The method of claim 12 wherein the lubricant composition comprises a silicone.

14. The method of claim 13 wherein the lubricant composition comprises an aminoalkyl siloxane.

15. The method of claim 14 wherein the lubricant composition further comprises a second siloxane that is copolymerizable with the aminoalkyl siloxane.

16. The method of claim 14 wherein the lubricant composition further comprises a second siloxane that does not copolymerize with the aminoalkyl siloxane.

17. The method of claim 14 further comprising the step of curing the aminoalkyl siloxane.

18. The method of claim 13 wherein the lubricant composition comprises a polydimethylsiloxane having amino and alkoxy functional groups.

19. The method of claim 13 wherein the lubricant composition comprises a polydimethylsiloxane and hexane.

20. The method of claim 17 wherein the step of curing the lubricant composition comprises:
   subjecting the lubricant composition to an atmosphere of from about 20% to about 80% relative humidity, at a temperature from about 10° C. to about 50° C. for a time period ranging from about 1 hour to about 6 hours; and,
   heating to a temperature of from about 100° C. to about 200° C. for a time period ranging from about 2 hours to about 48 hours to effectively polymerize the lubricant composition.

21. A method for coating a surgical needle comprising the steps of:
   providing a surgical needle having a surface;
   subjecting the surface of the needle to a plasma polymerization process wherein a polymer coating is formed on the needle surface from a hydrocyclosiloxane monomer of the general formula

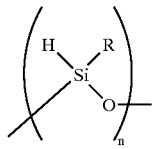

where R is an aliphatic group and n is an integer from 2 to about 10, preferably 4 to 6;
   adding an amine group onto the polymer coating by subjecting the needle to a gas containing a monomer selected from the group consisting essentially of unsaturated N-protected amines, unsaturated N-unprotected amines, N-protected cyclic aliphatic amines, and N-unprotected cyclic aliphatic amines, to produce an amine grafted polymer coating; and
   contacting the amine grafted polymer coating with a carbonate-based polyalkylene oxide compound of the formula

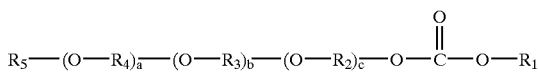

wherein $R_1$ is selected from an N-benzotriazole group, an N-2-pyrrolidinone group, or a 2-oxypyrimidine group; $R_2$, $R_3$ and $R_4$ are independently selected alkylene groups of about 2 to about 3 carbon atoms and may be the same or different; $R_5$ is selected from hydrogen, methyl, a carbonyloxy-N-benzotriazole group, a carbonyloxy-N-2-pyrrolidinone group, and a carbonyl-2-oxypyrimidine group; a is an integer from 1 to 1000 and each of b and c is an integer from 0 to 1000, where a+b+c is an integer from 3 to 1000 to produce a polyoxyalkylene modified polymer coating.

22. The method of claim 21 wherein said hydrocyclosiloxane monomer is selected from the group consisting of 1,3,5,7-tetramethylcyclotetrasiloxane; 1,3,5,7,9-pentamethylhydrocyclopentasiloxane; 1,3,5,7,9,11-hexamethylhydrocyclohexasiloxane and a mixture of 1,3,5,7,9-pentamethylcyclopentasiloxane and 1,3,5,6,9,11-hexamethylcyclohexasiloxane monomers.

23. The method of claim 21 wherein the unsaturated or cyclic amine is copolymerized with the hydrocyclosiloxane monomer onto the needle surface.

24. The method of claim 21 wherein the unsaturated or cyclic amine is plasma grafted onto the polymer coating on the needle surface.

25. The method of claim 21 wherein said unsaturated or cyclic amine is N-trimethylsilylallylamine.

26. The method of claim 21 wherein said carbonate-based polyalkylene oxide compound is polyoxyethylene bis-(N-hydroxybenzotriazolyl) carbonate.

27. The method of claim 21 further comprising the step of subjecting the needle surface to plasma etching prior to the plasma polymerization process.

28. The method of claim 27 wherein the plasma etching comprises treating the needle surface with an ammonia/oxygen plasma.

29. The method of claim 21 further comprising applying a lubricant composition to the polyoxyalkylene modified polymer coating.

30. The method of claim 29 wherein the lubricant composition comprises a silicone.

31. The method of claim 30 wherein the lubricant composition comprises an aminoalkyl siloxane.

32. The method of claim 31 wherein the lubricant composition further comprises a second siloxane that is copolymerizable with the aminoalkyl siloxane.

33. The method of claim 31 wherein the lubricant composition further comprises a second siloxane that does not copolymerize with the aminoalkyl siloxane.

34. The method of claim 31 further comprising the step of curing the aminoalkyl siloxane.

35. The method of claim 29 wherein the lubricant composition comprises a polydimethylsiloxane having amino and alkoxy functional groups.

36. The method of claim 29 wherein the lubricant composition comprises a polydimethylsiloxane and hexane.

37. The method of claim 34 wherein the step of curing the lubricant composition comprises:
subjecting the lubricant composition to an atmosphere of from about 20% to about 80% relative humidity, at a temperature from about 10° C. to about 50° C. for a time period ranging from about 1 hour to about 6 hours; and,
heating to a temperature of from about 100° C. to about 200° C. for a time period ranging from about 2 hours to about 48 hours to effectively polymerize the lubricant composition.

38. A coated surgical needle comprising:
a surgical needle having an outer surface; and
a plasma polymerized polymer coating formed on at least a portion of said outer surface of said surgical needle.

39. A coated surgical needle as in claim 38 further comprising a silicone-containing coating applied to the plasma polymerized polymer coating.

40. A coated surgical needle as in claim 39 wherein the silicone-containing coating comprises an aminoalkyl siloxane.

41. A coated surgical needle as in claim 39 wherein the silicone-containing coating comprises a copolymer of an aminoalkyl siloxane and a second siliconization material.

42. A coated surgical needle comprising:
a surgical needle having an outer surface;
a polymer coating formed on at least a portion of said outer surface of said surgical needle, said polymer coating including a plasma polymerized amine substituted polymer coating having polyoxyalkylene groups bonded thereto.

43. A coated surgical needle as in claim 42 further comprising a silicone-containing coating applied to the amine grafted polymer coating having polyoxyalkylene groups.

44. A coated surgical needle as in claim 42 wherein the silicone-containing coating comprises an aminoalkyl siloxane.

45. A coated surgical needle as in claim 42 wherein the silicone-containing coating comprises a copolymer of an aminoalkyl siloxane and a second siliconization material.

46. A surgical needle having reduced penetration force comprising:
a surgical needle having a polymer coating formed by a plasma polymerization process; and
a silicone-containing coating over at least a portion of the polymer coating,
whereby the surgical needle has a penetration force on a fifth pass through tissue that is at least 10% less than the penetration force on a fifth pass through tissue of a needle having the same silicone-containing coating on the same surgical needle having no polymer coating.

47. A surgical needle as in claim 46 wherein the silicone-containing coating comprises an aminoalkyl siloxane.

48. A surgical needle as in claim 46 wherein the silicone-containing coating comprises a copolymer of an aminoalkyl siloxane and a second siliconization material.

* * * * *